(12) United States Patent
Van Ness et al.

(10) Patent No.: US 6,248,521 B1
(45) Date of Patent: Jun. 19, 2001

(54) AMPLIFICATION AND OTHER ENZYMATIC REACTIONS PERFORMED ON NUCLEIC ACID ARRAYS

(75) Inventors: Jeffrey Van Ness; Kristen Moynihan, both of Seattle; John C. Tabone, Bothell, all of WA (US)

(73) Assignee: Qiagen Genomics, Inc., Bothell, WA (US)

( * ) Notice: Subject to any disclaimer, the term of this patent is extended or adjusted under 35 U.S.C. 154(b) by 0 days.

(21) Appl. No.: 09/120,501

(22) Filed: Jul. 21, 1998

Related U.S. Application Data

(60) Provisional application No. 60/053,428, filed on Jul. 22, 1997, now abandoned.

(51) Int. Cl.[7] .............................. C12Q 1/68; C12P 19/34; C12P 21/04; B05D 3/04

(52) U.S. Cl. .......................... 435/6; 435/91.2; 435/71.1; 427/333

(58) Field of Search .......................... 435/6, 91.2, 71.1; 427/333

(56) References Cited

U.S. PATENT DOCUMENTS

| | | |
|---|---|---|
| 4,020,698 | 5/1977 | D'Autry .............................. 73/425.6 |
| 4,827,780 | 5/1989 | Sarrine et al. ..................... 73/864.21 |
| 4,981,783 | 1/1991 | Augenlicht ............................... 435/6 |
| 5,143,854 | 9/1992 | Pirrung et al. ....................... 436/518 |
| 5,384,261 | 1/1995 | Winkler et al. ...................... 436/518 |
| 5,436,327 | 7/1995 | Southern et al. ................. 536/25.34 |
| 5,474,796 | 12/1995 | Brennan .............................. 427/2.13 |
| 5,512,462 * | 4/1996 | Cheng ................................ 435/91.2 |
| 5,525,464 | 6/1996 | Drmanac et al. ........................ 435/6 |
| 5,547,835 * | 8/1996 | Koster et al. ............................. 435/6 |
| 5,605,798 * | 2/1997 | Koster ...................................... 435/6 |
| 5,658,802 | 8/1997 | Hayes et al. ......................... 436/518 |
| 5,709,668 | 1/1998 | Wacks .................................. 604/232 |
| 5,741,554 | 4/1998 | Tisone ................................... 427/424 |
| 5,741,637 * | 4/1998 | Rueger et al. ............................. 435/6 |
| 5,744,305 | 4/1998 | Fodor et al. .............................. 435/6 |
| 5,770,151 | 6/1998 | Roach et al. ............................ 422/63 |
| 5,770,367 | 6/1998 | Southern et al. ......................... 435/6 |
| 5,800,992 | 9/1998 | Fodor et al. .............................. 435/6 |
| 5,807,522 | 9/1998 | Brown et al. .......................... 422/50 |
| 5,846,710 * | 12/1998 | Bajaj ....................................... 435/6 |
| 5,919,523 * | 7/1999 | Sundberg et al. .................... 427/333 |
| 6,101,946 | 8/2000 | Martinsky ............................ 101/494 |

FOREIGN PATENT DOCUMENTS

| | | |
|---|---|---|
| WO 90/13666 | 11/1990 | (WO) . |
| WO 91/07505 | 5/1991 | (WO) . |
| WO 93/19207 | 9/1993 | (WO) . |
| WO 94/29484 | 12/1994 | (WO) . |
| WO 95/20679 | 8/1995 | (WO) . |
| WO 95/33073 | 12/1995 | (WO) . |
| WO 96/04404 | 2/1996 | (WO) . |
| WO 96/31622 | 10/1996 | (WO) . |

OTHER PUBLICATIONS

Lu et al., "Use of glycerol for enhanced efficiency and specificity of PCR amplification", Trends in Genetics, vol. 9(9), p. 297, Sep. 1993.*

Blanchard et al., (1996), "High–density oligonucleoyide arrays," *Biosens. Bioelectron. 11*: 687–690.

Chee et al., (1996), "Accessing genetic information with high–density DNA arrays," *Science 274*: 610–614.

Chu et al., (1998), "The transcriptional program of sporulation in budding yeast," *Science 282*, 699–705.

(List continued on next page.)

*Primary Examiner*—Jeffrey Fredman
*Assistant Examiner*—Arun Chakrabarti
(74) *Attorney, Agent, or Firm*—Seed Intellectual Property Law Group PLLC

(57) ABSTRACT

The present invention provide methods and an apparatus for performing amplification and other enzymatic reactions on nucleic acid molecules that have been printed onto a solid substrate, such as a silicon wafer or glass slide.

41 Claims, 5 Drawing Sheets-

OTHER PUBLICATIONS

Cronin et al. (1996), "Cystic Fibrosis Mutation Detection by Hybridization to Light–Generated DNA Probe Arrays," *Human Mutation 7*: 244–255.

DeRisi et al. (1996), "Use of a cDNA microarray to analyze gene expression patterns in human cancer," *Nat Genet 14*: 457–460.

DeRisi et al., (1997), "Exploring the metabolic and genetic control of gene expression on a genomic scale," *Science 278*: 680–686.

de Saizieu et al., (1998), "Bacterial transcript imaging by hybridization of total RNA to oligonucleotide arrays," *Nature Biotech. 16*: 45–48.

Drmanac et al., (1998), "Accurate sequencing by hybridization for DNA diagnostics and individual genomics," *Nature Biotech. 16*: 54–58.

Fodor et al., (1991), "Light–directed, spatially addressable parallel chemical synthesis," *Science 251*: 767–773.

Hacia et al., (1996), "Detection of heterozygous mutations in BRCA1 using high density oligonucleotide arrays and two–colour fluorescence analysis," *Nature Genet. 14*: 441–447.

Heller et al., (1997), "Discovery and analysis of inflammatory disease–related genes using cDNA microarrays," *Proc Natl Acad Sci USA. 94*: 2150–2155.

Khrapko et al., (1991), "Hybridization of DNA with oligonucleotides immobilized in gel: a convenient method for detecting single base substitutions," *Molecular Biology 25*: 581–591.

Kozal et al., (1996), "Extensive polymorphisms observed in HIV–1 clade B protease gene using high–density oligonucleotide arrays," *Nature Med. 2*: 753–759.

Lashkari et al., (1997), "Yeast microarrays for genome wide parallel genetic and gene expression analysis," *Proc. Natl. Acad. Sci. USA 94*: 13057–13062.

Lemieux et al., (1998) "Overview of DNA Chip Technology," *Molecular Breeding 4*: 277–289.

Lockhart et al., (1996), "Expression Monitoring by Hybridization to High–Density Oligonucleotide Arrays," *Nature Biotechnology 14*: 1675–1680.

Maier et al. (1994), "Application of robotic technology to automated sequence fingerprint analysis by oligonucleotide hybridisation," Summary.

Pease et al., (1994), "Light–generated oligonucleotide arrays for rapid DNA sequence analysis," *Proc. Natl. Acad. Sci. USA 91*: 5022–5026.

Sapolsky and Lipshutz, (1996), "Mapping Genomic Library Clones Using Oligonucleotide Arrays," *Genomics 33*: 445–456.

Schena et al., (1995), "Quantitative monitoring of gene expression patterns with a complementary DNA microarray," *Science 270*:467–470.

Schena, M., (1996), "Genome Analysis with Gene Expression Microarrays," *BioEssays 18*: 427–431.

Schena et al., (1996), "Parallel human genome analysis: microarray–based expression montitoring of 1000 gene," *Proc Natl Acad Sci USA 93*: 10614–10619.

Schena et al., (1998), "Microarrays: Biotechnology's discovery platform for functional genomics," *Trends Biotech. 16*: 301–306.

Schena and Davis, (1998), "Parallel Analysis with Biological Chips. in PCR Methods Manual," Academic Press (San Diego), in press.

Shalon et al., (1996), "A DNA micro–array system for analyzing complex DNA samples using two–color fluorescent probe hybridization," *Genome Research 6*: 639–645.

Shoemaker et al., (1996), "Quantitative phenotypic analysis of yeast deletion mutants using a highly parallel molecular bar–coding strategy," *Nature Genetics 14*: 450–456.

Wodicka et al., (1997), "Genome–wide expression monitoring in *Saccharomyces cerevisiae*," *Nature Biotech. 15*: 1359–1367.

Yershov et al. (1996), "DNA analysis and diagnostics on oligonucleotide microchips," *Proc. Natl. Acad. Sci. USA 93*: 4913–4918.

cmgm.stanford.edu/pbrown/mguide, Sep. 12, 2000 and cmgm.stanford.edu/pbrown/mguide/tips. Sep. 12, 2000.

* cited by examiner

Visible light illumination:

Fluorescence illumination:

Layout of arrayed oligo solutions
(72 spots per grid)

Pattern produced when grids were
hybridized to the complement of oligo #1

Pattern produced when grids were
hybridized to the complement of oligo #2

AMPLIFICATION AND OTHER ENZYMATIC REACTIONS PERFORMED ON NUCLEIC ACID ARRAYS

CROSS-REFERENCE TO RELATED APPLICATION

The present application claims the benefit of U.S. Provisional Patent Application No. 60/053,428, filed Jul. 22, 1997, now abandoned.

TECHNICAL FIELD

This invention relates generally to enzymatic reactions performed on nucleic acids that are arrayed on a solid substrate, and in particular, to amplification of nucleic acids that are arrayed.

BACKGROUND OF THE INVENTION

Replicate arrays of biological agents have been used to facilitate parallel testing of many samples. For example, sterile velvet cloths and a piston-ring apparatus has long been used to make replicates of bacterial and yeast colonies to agar plates each containing a different growth medium, as a means of rapidly screening a large number of independent colonies for different growth phenotypes (Lederberg and Lederberg, *J. Bacteriol.* 63 :399, 1952). Likewise, 96-well microtiter plates are used to organize and store in an easily accessed fashion large numbers of e.g. cell lines, virus isolates representing recombinant DNA libraries, or monoclonal antibody cell lines.

The advent of large scale genomic projects and the increasing use of molecular diagnostics has necessitated the development of large volume throughput methods for screening nucleic acids. Recently, methods have been developed to synthesize large arrays of short oligodeoxynucleotides (ODNs) bound to a glass or silicon surface that represent all, or a subset of all, possible nucleotide sequences (Maskos and Southern, *Nucl. Acids Res.* 20: 1675, 1992). These ODN arrays have been made used to perform DNA sequence analysis by hybridization (Southern et al., *Genomics* 13: 1008, 1992; Drmanac et al., *Science* 260: 1649, 1993), determine expression profiles, screen for mutations and the like. In all these uses, the ODNs are covalently attached to the surface of the substrate. However, some useful screening techniques and assays are not readily adaptable to a format in which ODNs are immobilized.

In particular, amplification of nucleic acids, notably the polymerase chain reaction (PCR) and its many variations, has found wide application to many different many biological problems and is not easily moved to a format where the ODNs are immobilized. In its standard format, PCR has two major limitations to its commercial utilization: the cost of reagents and the ability to automate the process. Reagent costs, especially DNA polymerase, can be lowered if the total volume of each reaction is decreased. An accurate and reliable means to array small volumes of reagents using a robotically controlled pin tool would miniaturize the reactions. Additional hurdles to moving amplification to an array format include preventing evaporation during heating and cooling cycles and preventing spreading and merging of the reactions on the array.

The present invention discloses methods and compositions for performing amplification and other enzymatic reactions in an array format without the need to immobilize the components, and further provides other related advantages.

SUMMARY OF THE INVENTION

Within one aspect of the present invention, methods of amplifying nucleic acid molecules from a template are provided comprising (a) mixing single-stranded nucleic acid templates on a solid substrate with a solution comprising an oligonucleotide primer that hybridizes to the templates and a DNA polymerase, wherein the mixing occurs in discrete areas on the substrate, and wherein the solution remains in the discrete areas; (b) synthesizing a complementary strand to the template to form a duplex; (c) denaturing the duplex; and (d) synthesizing complementary strands to the template, therefrom amplifying nucleic acid molecules; wherein mixing, synthesizing, and denaturing are conducted at dew point. The solid substrate may be a silicon wafer or glass slide. The templates may be covalently attached to the solid substrate or deposited on the surface of the substrate. The template may be uniformly applied to the entire array prior to mixing or applied individually to each discrete area on the substrate. When applied individually, preferably the applying is performed using spring probes. In a most preferred embodiment, an apparatus is used to control the dew point.

Within a related aspect, the method of amplifying uses a first oligonucleotide primer that hybridizes to the templates, a second oligonucleotide primer that hybridizes to a complementary strand of the template, and after sythesizing, denaturing the duplex; and synthesizing complementary strands to the template and the complementary strand of the template, therefrom amplifying nucleic acid molecules.

In preferred embodiments, the denaturing and synthesizing steps are performed multiple times. In other preferred embodiments, the solution contains a compound that confers viscosity, such as glycerol or a sugar. In other preferred embodiments, the DNA polymerase is a thermostable polymerase and synthesis and denaturation are performed at different temperatures.

In yet other preferred embodiments, the method further comprises detecting the duplexes. Most preferably, the oligonucleotide primers are labeled with a tag that is detectable by non-fluorescent spectrometry or potentiometry, and preferably by mass spectrometry, infrared spectrometry, ultra-violet spectrometry, or poteniostatic amperometry.

In another aspect, a method of synthesizing a nucleic acid molecule from a template is provided, comprising (a) mixing single-stranded nucleic acid templates on a solid substrate with a solution comprising an oligonucleotide primer that hybridizes to the templates and a DNA polymerase, wherein the mixing occurs in a discrete area of an array, and wherein the solution remains in discrete areas; and (b) synthesizing a complementary strand to the template to form a duplex, wherein mixing and synthesis are performed at dew point, wherein dew point is maintained or achieved by an apparatus, comprising: a container capable of being pressurized; a heating device; a means for generating pressure; and a means for generating saturated steam; wherein the heating device, pressure generating means, and steam generating means are controllable.

In yet another aspect, a method of detecting a single base alteration in a nucleic acid molecule, is provided comprising (a) mixing single-stranded nucleic acid molecules on a solid substrate with a solution comprising a first and a second oligonucleotides that hybridize to the nucleic acid molecules and a DNA ligase, wherein the mixing occurs in a discrete area of an array, and wherein the solution remains in the discrete areas; and (b) detecting a ligation product; wherein the first and second oligonucleotides will not ligate when there is a single base alteration at the junction base on the nucleic acid molecule, wherein mixing is performed at dew point.

In yet another aspect, a method of performing single nucleotide extension assay is provided, comprising (a) mixing oligonucleotides on a solid substrate with a solution comprising single-stranded nucleic acid molecules that hybridize to the oligonucleotides, a single nucleotide, and a DNA polymerase, wherein the mixing occurs in discrete areas of the substrate, and wherein the solution remains in discrete areas; and (b) detecting an extension product of the oligonucleotide; wherein the oligonucleotide will be extended only when the single nucleotide is complementary to the nucleotide adjacent to the hybridized oligonucleotide, wherein mixing is performed at dew point.

In other aspects, the invention provides a kit for genotyping, comprising a solid substrate containing an array of labeled oligonucleotide primer pairs. In preferred embodiments, the kit further comprises nucleic acid templates and a viscous solution.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

The methods and kits of the present invention may include tagged biomolecules, for example, oligonucleotides covalently bonded to cleavable tags. Exemplary tagged biomolecules, and assays which may use the same, are described in U.S. patent application Ser. Nos. 08/786,835; 08/786,834 and 08/787,521, each filed on Jan. 22, 1997, as well as in three U.S. continuation-in-part patent applications having Application Ser. Nos. 08/898,180; 08/898,564; and 08/898,501, each filed Jul. 22, 1997 and PCT International Publication Nos. WO 97/27331; WO 97/27325; and WO 97/27327. These six U.S. Patent Applications and three PCT International Publications are each hereby fully incorporated herein by reference in their entireties.

The methods and kits of the present invention may be used in conjunction with arrays that contain more than one oligonucleotide sequence within an element (or "first region"). Biomolecule arrays containing more than one oligonucleotide sequence within an element, and uses thereof, are described in our U.S. patent application Ser. No. 09/120,688 titled "Multiple Functionalities Within An Array Element And Uses Thereof" filed concurrently herewith, which claims the priority benefit of U.S. Provisional Patent Application No. 60/053,436 filed Jul. 22, 1997, both of which are hereby fully incorporated herein by reference in their entireties.

Biomolecule arrays that may be used in conjunction with the methods and kits of the present invention may be prepared according to techniques disclosed in our U.S. patent application Ser. No. 09/120,689 titled "Apparatus and Methods For Arraying Solution Onto A Solid Support" filed concurrently herewith, which claims the priority benefit of U.S. Provisional Patent Application No. 60/053,435 filed Jul. 22, 1997, both of which are hereby fully incorporated herein by reference in their entireties.

Biomolecule arrays that may be used in conjunction with the methods and kits of the present invention may be prepared according to techniques as disclosed in our U.S. patent application Ser. No. 09/120,386 titled "Polyethylenimine-Based Biomolecule Arrays" filed concurrently herewith, which claims the priority benefit of U.S. Provisional Patent Application No. 60/053,352 filed Jul. 22, 1997, both being fully incorporated herein by reference in their entireties.

Computer systems and methods for correlating data, as disclosed in U.S. patent application Ser. No. 09/120,686 titled "Computer Method and System For Correlating Data" filed concurrently herewith, which claims the priority benefit of U.S. Provisional Patent Application No. 60/053,429 filed Jul. 22, 1997 (both being fully incorporated herein by reference in their entireties) may be used in combination with the amplification and other enzymatic reactions performed on nucleic acid arrays as described herein.

DETAILED DESCRIPTION OF THE INVENTION

Figure 1A:
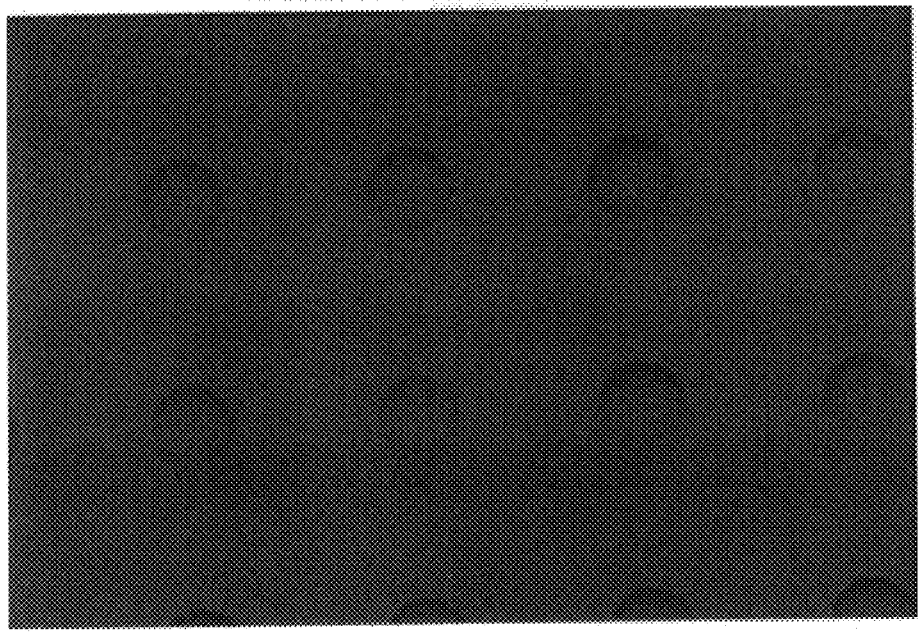
FIG. 1 shows photomicrographs of arrayed microspheres taken under visible light illumination (top panel) and fluorescence illumination (bottom panel).

As noted above, the present invention provides methods and apparatus for amplifying nucleic acid molecules from a template as well as methods and apparatus for performing enzymatic assays on nucleic acid molecules. These methods are generally performed on an array of nucleic acid molecules made as described herein. In the present invention, these methods are performed in an apparatus that controls dew point.

I. Application of Templates to Solid Substrate

A. Substrate preparation

A substrate for arrays is prepared from a suitable material. The substrate is preferably rigid and preferably has a surface that is substantially flat. In some embodiments, the surface may have raised rigids to delineate regions. Typical substrates are silicon wafers and borosilicate slides (e.g., microscope glass slides), although other materials known in the art may be substituted. An example of a particularly useful solid support is a silicon wafer that is typically used in the electronics industry in the construction of semicomductors. The wafers are highly polished and reflective on one side and can be easily coated with various linkers, such as poly(ethyleneimine) using silane chemistry. Wafers are commercially available from companies such as WaferNet, San Jose, Calif.

Nucleic acid molecules or other biopolymers, such as peptides, may either be synthesized in situ, i.e., on the solid substrate, or synthesized elsewhere and applied to the substrate. Alternatively, substrates with oligonucleotides already present in arrays can be purchased (e.g., Affymetrix, Palo Alto, Calif). Many suitable methods for synthesizing nucleic acids on a solid substrate, such as a silicon wafer, are readily available. These methods rely on standard protocols, such as phosphoramidite chemistry, to synthesize an oligonucleotide. Nucleic acids and peptides may also be synthesized in an automated fashion using a commercially available machine. A preferred method is to prepare the nucleic acid molecules and apply them to the substrate. In certain embodiments, the molecules are covalently attached to the substrate. In preferred embodiments, the nucleic acids are deposited on the solid substrate and are not covalently attached.

In certain embodiments, the surface of the substrate is prepared for the oligonucleotides. The surface may be prepared by, for example, coating with a chemical that increases or decreases the hydrophobicity or coating with a chemical that allows covalent linkage of the nucleic acid molecules or other polymeric sequences. Some chemical coatings may both alter the hydrophobicity and allow covalent linkage. Hydrophobicity on a solid substrate may readily be increased by silane treatment or other treatments known in the art. A chemical that allows covalent linkage is generally referred to as a linker. These linker molecules adhere to the surface of the substrate and comprise a functional group that reacts with biomolecules. Many such linkers are readily available. For example, solid supports are modified with photolabile-protected hydroxyl groups (see, U.S. Pat. Nos. 5,412,087; 5,571,639; 5,593,839), alkoxy or aliphatic derivatized hydroxyl groups (U.S. Pat. No. 5,436,327), or other chemicals (see e.g., U.S. Pat. No. 5,445,934; EP Patent No. EP-B1-0,373,203; U.S. Pat. No. 5,474,796; U.S. Pat. No. 5,202,231)

A preferred coating that both decreases hydrophobicity and provides linkers is poly(ethyleneimine). In addition, poly(ethyleneimine) (PEI) coated solid substrates also have the added benefit of long shelf life stability. The coating of silicon wafers and glass slides with polymers such as poly(ethyleneimine) can be performed in-house or through companies such as Cel Associates (Houston, Tex.). Glass slides can also be coated with a reflective material or coated with PEI using silane chemistry. The PEI coating permits the covalent attachment of single or double stranded oligonuclceotides, single or double stranded long DNA molecules or fragments or any other amine-containing biomolecules to the solid support. Oligonucleotides may be covalently attached at the 5' using a hexylamine modification, which places a primary amine at the 5'-end of the oligonucleotide. The 5'-amine on the oligonucleotide may then be reacted with a cross-linker, such that the oligonucleotide is covalently attached to the polymer coating on the solid support.

Any nucleic acid type can be covalently attached to a PEI coated surface as long as the nucleic acid contains a primary amine. Amplified products (e.g, by PCR) may be modified to contain a primary amine by using 5'-hexylamine-conjugated primers. Amine groups may be introduced into amplified products and other nucleic acid duplexes by nick translation using allyl-dUTP (Sigma, St. Louis, Mo.). As well, amines may be introduced into nucleic acids by polymerases, such as terminal transferase, or by ligation of short amine-containing oligonucleotides. Other suitable methods known in the art may be substituted.

Cross linkers suitable for amine groups are generally commercially available (see, e.g., Pierce, Rockford, Ill.). A typical cross-linker is trichlorotriazine (cyanuric chloride) (Van Ness et al., *Nucleic Acids Res.* 19: 3345–3350, 1991). Briefly, an excess of cyanuric chloride is added to the oligonucleotide solution (e.g., a 10 to 1000-fold molar excess of cyanuric chloride over amines) at a typical oligonucleotide concentration of 0.01 to 1 $\mu$g/ml, and preferably about 0.1 $\mu$g/ml. The reaction is buffered using common buffers such as sodium phosphate, sodium borate, sodium carbonate, or Tris HCL at a pH range from 7.0 to 9.0. The preferred buffer is freshly prepared 0.2 M NaBorate at pH 8.3 to pH 8.5. Ten $\mu$l of 15 mg/ml solution of cyanuric chloride is added and allowed to react with constant agitation from 1 to 12 hours and preferably approximately 1 hour. Reaction temperature may range from 20 to 50° C. with the preferred reaction temperature at 25° C. (or ambient temperature).

When cyanuric chloride is used as a cross linker, there is no need to remove the excess crosslinker prior to printing the nucleic acids on a solid substrate. Excess cyanuric chloride in the reaction mixture does not interfer or compete with the covalent attachment of the nucleic acid or oligonucleotides to the PEI coated solid support, because of an excess of amines on the solid support over the number of cyanuric chloride molecules. In a preferred embodiment, cross-linked oligonucleotides are not purified prior to the printing step.

If the nucleic acids or other amine-containing polymers are to be covalently attached, the activated polymers are allowed to react with the solid support for 1 to 20 hours at 20 to 50° C. and preferably for 1 hour at 25° C. The free amines on the solid support are then capped to prevent non-specific attachment of other nucleic acids. Capping is accomplished by reacting the solid support with 0.1 to 2.0 M succinic anhydride, and preferably 1.0 M succinic anhydride in 70% m-pyrol and 0.1 M NaBorate, for 15 minutes to 4 hours with a preferred reaction time of 30 minutes at 25° C. The solid support is then incubated in a 0.1 to 10.0 M NaBorate, pH 7 to pH 9 (preferably 0.1 M NaBorate pH 8.3) solution containing 0.1 to 5 M glycine (preferably 0.2 M glycine) and then washed with detergent-containing solution. This "caps" any dichloro-triazine that may be covalently bound to the PEI surface. Preferably, the solid support is further heated to 95° C. in 0.01 M NaCl, 0.05 M EDTA and 10 mM Tris pH 8.0 for 5 minutes to remove any non-covalently attached nucleic acids. In the case where double stranded nucleic acids are printed onto a solid substrate, this step also converts (denatures) the double strand to a single strand form.

B. Methods of applying nucleic acid molecules to solid substrates

Oligonucleotides, nucleic acid molecules or other biopolymers are "printed" (delivered or applied) on a solid substrate. In preferred embodiments, the polymers are applied in a regular pattern or array. In other preferred embodiments, the polymers are applied to the entire area of the solid substrate and allowed to dry, after which additional polymers, buffers, enzymes and the like are applied in an array pattern. The polymers may be applied to the substrate in a buffered salt solution without detergents, such as 10 mM Tris, 50 mM NaCl, and 5 mM EDTA, using a pipettor, nylon roller, stamps, or the like.

A variety of printing methods are available for applying nucleic acids, such as oligonucleotides or DNA fragments, to a solid substrate in an array pattern. As a general guideline, the delivery mechanism must be capable of positioning very small amounts of liquids (e.g., nanoliters) in small regions (e.g., 10–200 $\mu$m diameter dots) where the regions are very close to one another (e.g., 25–500 $\mu$m center to center distance). Preferably the printing technique is amenable to automation. One such technique is ink-jet printing using multiple heads. Very fine pipettes may also be used. A preferred means of printing is using spring probes as described herein.

Sample pick-up, transfer and micro-droplet deposition is greatly enhanced when using a liquid transfer device that has a hydrophilic surface, especially when that device is a modified spring probe. Spring probes are made hydrophilic through the use of chemical agents acting to modify the surface of the probe or through coating the probe with a hydrophilic substance. In a preferred method, the tip of the spring probe is soaked in a 25–200 mM solution of 1,4-dithiothreitol, 0.1 M sodium borate for 15 min to 2 hrs. Dithiothreitol reacts with gold surfaces through a thiol-gold coordination, which essentially hydroxylates the surface, making it hydrophilic.

The hydrophilic surface promotes an even coating of sample when the spring probe is dipped in solution. The fluted probe becomes evenly and consistently loaded with liquid drawn to the probe surface by its hydrophilic nature. Solutions with viscosity enhancing chemicals, such as glycerol, provide especially improved handling capabilities using hydrophilic surfaces. With these solutions, the glycerol adheres to the probe even as it pulled from the source of liquid. As a sample is transferred from its source to a solid support, the hydrophilic surface of the probe continues to benefit liquid handling by retaining the sample being transferred and inhibiting the sample from randomly dripping or running during transport. When a sample bearing spring probe comes into contact with a solid support, the sample is deposited from the tip of the spring probe onto the surface of the solid support, especially in the case of a sample containing a viscosity enhancing solution. The size of the areas spotted generally range from 10–200 $\mu$m with a typical center to center distance of 25–500 $\mu$m.

Briefly, in a typical procedure, a solution of the nucleic acid is uniformly mixed in 57% glycerol and then printed onto the solid support. Within the context of this invention, the biopolymers may be either nucleic acid molecules or protein molecules. When nucleic acids are used, they may comprise single or double stranded DNA, single or double stranded RNA, oligonucleotides, hybrid DNA-RNA molecules or duplexes, PNA nucleic acids with a protein backbone and the like.

II. Reaction Components and Conditions

As noted above, the present invention provides methods for amplifying nucleic acids on a solid substrate as well as other enzymatic reactions. As noted above, the nucleic acids may be covalently attached to the surface of the substrate or may be deposited on the substrate without attachment. Typically, the template for amplification is printed first and reagents necessary for amplification or other enzymatic reactions are subsequently added.

A. Reagents, buffers, cofactors, etc.

Each area of the array that undergoes a reaction has in addition to the template nucleic acids, the appropriate enzyme, and any other required components, including, but not limited to, oligonucleotide primers, nucleotides, buffers, cofactors, and the like. For example, an amplification reaction includes template, DNA polymerase, nucleotides (e.g., dATP, dCTP, dGTP, dTTP), oligonucleotide primers, and buffer containing a divalent cation, usually $Mg^{++}$.

Amplification reactions are based on primer extensions (e.g., polymerase chain reaction, see U.S. Pat. Nos. 4,683,195; 4,683,202; and 4,800,159, cycling probe technology, NASBA), ligation (LCR, ligation chain reaction), RNA amplification (see Lizardi et al., *Bio/Technology* 6:1197, 1988; Kramer et al., *Nature* 339:401, 1989; Lomeli et al., *Clin. Chem.* 35:1826, 1989; U.S. Pat. No. 3,786,600), differential display (Liang and Pardee, *Science*, 257: 967–971, 1992; Liang, et al., *Nucl. Acids Res.*, 22:5763–5757, 1994), and the like. Preferably, the amplification method is polymerase chain reaction with a thermostable DNA polymerase, such as Taq DNA polymerase, $Vent_R$®DNA polymerase, $Vent_R$®(exo-) DNA polymerase, Pfu DNA polymerase, and the like. For these enzymes, optimal buffers and divalent cations are well known. Oligonucleotide primers are preferably average G+C content and with non-pairing 3' ends. Oligonucleotide sequence will also depend in part upon the region to be amplified. Conditions and considerations for oligo design, buffer concentrations and cation concentrations are well known (see, e.g., Ausubel et al. *Current Protocols in Molecular Biology*, Greene Publishing, 1995; Innis et al., PCR *Protocols: A Guide to Methods and Applications*, Academic Press, 1990; Sambrook et al. *Molecular Cloning: A Laboratory Manual*, Cold Spring Harbor Press, 1987). The nucleotides are generally the four deoxynucleotides, dATP, dCTP, dGTP, and dTTP, but may also include derivatives or rare bases.

Other enzymatic reactions within the context of this invention include synthesis of a nucleic acid molecule from a template, oligonucleotide ligation assay to detect a single base alteration in a nucleic acid molecule and a single nucleotide extension assay. For each of these methods, suitable conditions are well known.

In addition, the reactions may contain other chemicals or components. (see U.S. application Ser. Nos. 08/719,132 and 60/026,621, and International Publication Number WO 98/13527 which claims priority to these two U.S. Applications, all of which are incorporated herein in their entireties). For example, a hybotrope may be added to improve annealing of an oligonucleotide primer to template. A hybotrope refers to any chemical that can increase the enthalpy of a nucleic acid duplex by 20% or more when referenced to a standard salt solution (i.e., 0.165 M NaCl). A chemical exhibits hybotropic properties when, as a solution an 18 bp oligonucleotide duplex that is 50% G+C has a helical-coil transition (HCT) of 15° C. or less. HCT is the difference between the temperatures at which 80% and 20% of the duplex is single-stranded. The temperature for annealing is then chosen to be the discrimination temperature, which is a temperature at which a hybridization reaction is performed that allows detectable discrimination between a mismatched duplex and a perfectly matched duplex. A range of temperatures satisfy criteria of a discrimination temperature.

In a preferred embodiment, the reactions are performed in a viscous solution. Such a solution preferably raises the dew point (i.e., lowers vapor pressure), has a high surface tension, and improves printing ability. The viscous solution must not substantially inhibit enzymatic activity. Preferably, enzyme activity is inhibited less than 1 to 20%. Suitable compounds to increase viscosity include glycerol and sugars. Preferably, glycerol is present at 20–100% and more preferably at 20–70%. Other suitable compounds may be identified by (a) determining enzyme activity in the presence of the compound, and (b) forming drops on a solid substrate, incubating at the reaction temperature, and observing that discrete drops (areas) remain. In general, the more hydrophobic the substrate surface, the lower the viscosity solution, and the more hydrophilic the substrate surface, the higher the viscosity solution.

B. Apparatus to maintain dew point

As noted above, the reactions are performed at dew point. Dew point, as used herein, refers to a temperature range where the droplet size does not change significantly. As described herein, an apparatus capable of controlling temperature, pressure, and water content may be used to maintain dew point.

As such, the reactions are conducted under pressure with a defined water content level that prevents the evaporation of water from the microdroplet. These conditions are achieved when there is an equilibrium state between the rate of evaporation of water from the microdroplet and the rate of condensation of water onto the microdroplet from the moist air overlying the substrate arrays. When this equilibrium is realized, the air is said to be saturated with respect to the planar surface of the array. The pressure (Ps) exerted by the water vapor is the saturation vapor pressure that must be maintained at any given temperature during the reaction. The magnitudes of the saturation vapor pressures depend only on temperature and increase rapidly with increasing temperature. That is, thermocycling amplification are conducted at essentially the dew points for all the temperatures achieved. For example, at 0° C., the absolute pressure of saturated steam is 0.0885 psi whereas at 100° C., the absolute pressure of saturated steam is 17.186 psi. Therefore, an apparatus should have the ability to maintain the dew point during all the temperature cycling that occurs during amplification or other enzymatic reaction. Essentially, saturated clean steam will be present in the "chamber." The apparatus is typically composed of a pressure chamber that contains the solid support, a controllable heating device, a means for generating pressure, and a means for generating saturated steam. All parameters are preferably controllable by computer. In other embodiments, the apparatus is a chamber with a means for generating pressure, a means for generating saturated steam and a seal, such that the chamber is sealed onto a controllable heating and cooling block (such as those commercially available). This modular apparatus is designed to fit formats of heating and cooling blocks of various sizes, e.g., from a 96-well plate size to a microscope slide.

Figure 5:
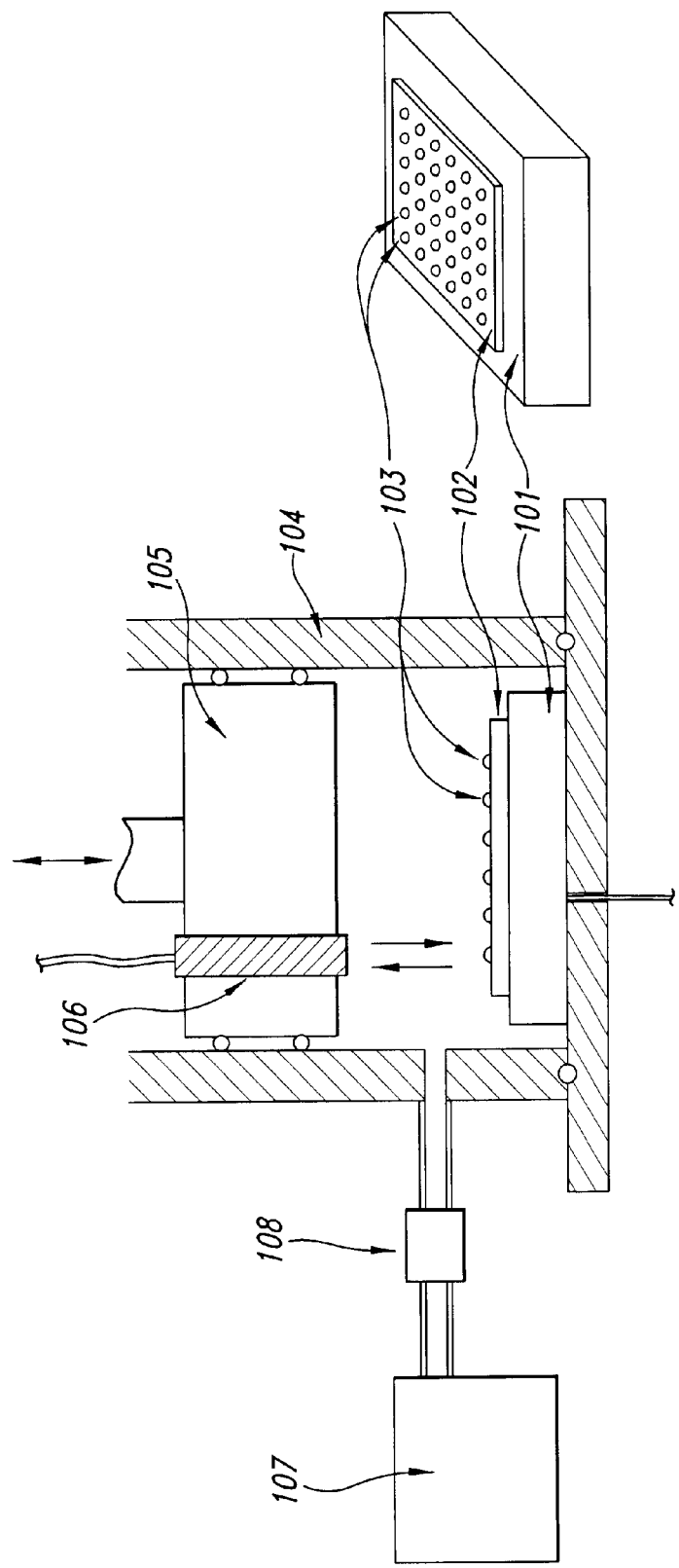
FIG. 5 is an illustration of an apparatus that controls dew point.

In a preferred embodiment, and in reference to FIG. 5, the invention provides a heating and cooling block 101 on which sits a glass cover slip 102, which contains the discrete areas of sample drops 103. The block is encased in an airtight cover 104 that forms a chamber, which has a piston 105 to adjust the internal pressure, a sensor 106 to measure dew point, and a source of water vapor 107.

In a preferred embodiment of the invention, the apparatus for opening the chamber, the temperature of the block, the position of the piston, and the valve are all under computer control. In one embodiment of the invention, the sensor (106) is a CCD camera and a light source behind a transparent section of the piston. In this embodiment, the size of one or more of the drops is continuously measured by imaging the drop(s) and comparing the drop image(s) to the image of a reference spot. The dew point is estimated by monitoring the drop size, and the pressure is adjusted to maintain the drops at their original size. The pressure is controlled by controlling the position of the piston. In another embodiment of the invention, the pressure is monitored using conventional sensors. In this embodiment, the pressure is varied to preset values which are based on the sample temperature and sample composition to fall within the predicted dew point range.

In a preferred embodiment of the invention, the source of water vapor (107) consists of source of dry gas which is passed through a water-saturated filter held at a constant temperature. The gas flowing out of the vapor source is saturated with water and at a controlled temperature. This gas is used to flush the chamber before the chamber is sealed, and serves to ensure that the composition of the atmosphere in the chamber is consistent and require evaporation from the samples to reach equilibrium.

III. Detection of Reaction Products

Reaction products may be detected by a variety of methods. Preferably, one of the reaction components is labeled. In amplification reactions, the oligonucleotide primers or the nucleotides are conveniently labeled. Preferably, the primers contain a label. In single nucleotide extension assay, the added nucleotide is generally labeled, in oligonucleotide ligation assay, one or more of the oligonucleotides are labeled, in other synthesis reactions, either the primer or the nucleotides are typically labeled.

Commonly employed labels include, but are not limited to, biotin, fluorescent molecules, radioactive molecules, chromogenic substrates, chemi-luminescence, and the like. The methods for biotinylating nucleic acids are well known in the art, as are methods for introducing fluorescent molecules and radioactive molecules into oligonucleotides and nucleotides.

When biotin is employed, it is detected by avidin, streptavidin or the like, which is conjugated to a detectable marker, such as an enzyme (e.g., horseradish peroxidase) or radioactive label (e.g., $^{32}P$, $^{35}S$, $^{33}P$). Enzyme conjugates are commercially available from, for example, Vector Laboratories (Burlingame, Calif.). Steptavidin binds with high affinity to biotin, unbound stretavidin is washed away, and the presence of horseradish peroxidase enzyme is then detected using a precipitating substrate in the presence of peroxide and appropriate buffers. The product may be detected using a microscope equipped with a visible light source and a CCD camera (Princeton Instrucments, Princeton, N.J.). With such an instrument, an image of approximately $10,000 \mu M \times 10,000 \mu M$ can be scanned at one time.

Detection methods are well known for fluorescent, radioactive, chemiluminescent, chromogenic labels, as well as other commonly used labels. Briefly, fluorescent labels can be identified and quantitated most directly by their absorption and fluorescence emission wavelengths and intensity. A microscope/camera setup using a light source of the appropriate wave length is a convenient means for detecting fluorescent label. Radioactive labels may be visualized by standard autoradiography, phophor image analysis or CCD detector. Other detection systems are available and known in the art. For labels such as biotin, radioactive, or fluorescent, the number of different reactions that can be detected at a single time is limited. For example, the use of four fluorescent molecules, such as commonly employed in DNA sequence analysis, limits anaylsis to four samples at a time. Essentially, because of this limitation, each reaction must be individually assessed when using these detector methods.

A more advantageous method of detection allows pooling of the sample reactions on at least one array and simultaneous detection of the products. By using a tag having a different molecular weight or other physical attribute in each reaction, the entire set of reaction products can be harvested together and analyzed. (see U.S. application Ser. Nos. 08/786,835; 08/786,834; 08/787,521; 08/898,180; 08/898,564; 08/898,501 and International Publication Nos. 97/27331; 97/27325 and 97/27327, all incorporated herein by reference in their entireties). Briefly, a "tag" molecule is used as a label. As used herein, a "tag" refers to a chemical moiety which is used to uniquely identify a "molecule of interest", and more specifically refers to the tag variable component as well as whatever may be bonded most closely to it in any of the tag reactant, tag component and tag moiety.

A tag useful in the present invention possesses several attributes: (1) It is capable of being distinguished from all other tags. This discrimination from other chemical moieties can be based on the chromatographic behavior of the tag (particularly after the cleavage reaction), its spectroscopic or potentiometric properties, or some combination thereof. Spectroscopic methods by which tags are usefully distinguished include mass spectroscopy (MS), infrared (IR), ultraviolet (UV), and fluorescence, where MS, IR and UV are preferred, and MS most preferred spectroscopic methods. Potentiometric amperometry is a preferred potentiometric method. (2) The tag is capable of being detected when present at $10^{-22}$ to $10^{-6}$ mole. (3) The tag possesses a chemical handle through which it can be attached to the MOI which the tag is intended to uniquely identify. The attachment may be made directly to the MOI, or indirectly through a "linker" group. (4) The tag is chemically stable toward all manipulations to which it is subjected, including attachment and cleavage from the MOI, and any manipulations of the MOI while the tag is attached to it. (5) The tag does not significantly interfere with the manipulations performed on the MOI while the tag is attached to it. For instance, if the tag is attached to an oligonucleotide, the tag must not significantly interfere with any hybridization or enzymatic reactions (e.g., amplification reactions) performed on the oligonucleotide.

A tag moiety that is intended to be detected by a certain spectroscopic or potentiometric method should possess properties which enhance the sensitivity and specificity of detection by that method. Typically, the tag moiety will have those properties because they have been designed into the tag variable component, which will typically constitute the major portion of the tag moiety. In the following discussion, the use of the word "tag" typically refers to the tag moiety (i.e., the cleavage product that contains the tag variable component), however can also be considered to refer to the tag variable component itself because that is the portion of the tag moiety which is typically responsible for providing the uniquely detectable properties. In compounds of the formula T—L—X, the "T" portion contains the tag variable component. Where the tag variable component has been designed to be characterized by, e.g., mass spectrometry, the "T" portion of T—L—X may be referred to as $T^{ms}$. Likewise, the cleavage product from T—L—X that contains T may be referred to as the $T^{ms}$-containing moiety. The following spectroscopic and potentiometric methods may be used to characterize $T^{ms}$-containing moieties.

Thus, within one aspect of the present invention, methods are provided for determining the identity of a nucleic acid molecule or fragment (or for detecting the presence of a selected nucleic acid molecule or fragment), comprising the steps of (a) generating tagged nucleic acid molecules from one or more selected target nucleic acid molecules, wherein a tag is correlative with a particular nucleic acid molecule and detectable by non-fluorescent spectrometry or potentiometry, (b) separating the tagged molecules by size (e.g., HPLC, electrophoresis) to remove labeled material not incorporated in the enzymatically generated product, (c) cleaving the tags from the tagged molecules, and (d) detecting the tags by non-fluorescent spectrometry or potentiometry, and therefrom determining the identity of the nucleic acid molecules. Examples of such technologies include for example mass spectrometry, infra-red spectrometry, potentiostatic amperometry or UV spectrometry.

IV. Uses

As noted above, the methods described herein may be used in a variety of ways. For example, amplification of template nucleic acids may be used for genotyping individuals, for mutation scanning, for determining expression profiles, and the like. Oligonucleotide ligation assays and single nucleotide extension assays may be used for mutation analysis, detection of a nucleic acid in a sample and the like. Each of these uses is briefly discussed below.

A. Genotyping

Within one preferred aspect of the present invention, methods are provided for genotyping a selected organism, comprising the steps of (a) generating tagged nucleic acid molecules from a selected target molecule, wherein a tag is correlative with a particular fragment and may be detected by non-fluorescent spectrometry or potentiometry, (b) separating the tagged molecules, (c) cleaving the tag from the tagged molecule, and (d) detecting the tag by non-fluorescent spectrometry or potentiometry, and therefrom determining the genotype of the organism. In other embodiments, the tag can be fluorescent, radioactive, etc.

Within another embodiment of the invention, methods are provided for determining the identity of a nucleic acid molecule, or for detecting a selecting nucleic acid molecule, in for example a biological sample, utilizing the technique of DNA fingerprinting. Briefly, such methods generally comprise the steps of generating a series of tagged nucleic acid fragments, followed by separation of the fragments by size. The size separation step can be accomplished, for example by gel electrophoresis (e.g., polyacrylamide gel electrophoresis) or preferably HPLC. The tags are then cleaved from the separated fragments, and then the tags are detected by the respective detection technology (e.g., mass spectrometry, infra-red spectrometry, potentiostatic amperometry or UV spectrometry).

Descriptions of many types of DNA sequence polymorphisms have provided the fundamental basis for the understanding of the structure of the human genome (Botstein et al., *Am. J. Human Genetics* 32:314, 1980; Donis-Keller, *Cell* 51:319, 1987; Weissenbach et al., *Nature* 359:794). The construction of extensive framework linkage maps has been facilitated by the use of these DNA polymorphisms and has provided a practical means for localization of disease genes by linkage. In addition to single base mutations, length variations of tandem repeats are also common in the genome, with at least tens of thousands of interspersed polymorphic sites (termed loci). There are two major groups of tandem repeat polymorphisms: minisatellites/variable number of tandem repeats (VNTRs), with typical repeat lengths of tens of base pairs and with tens to thousands of total repeat units, and microsatellites, with repeat lengths of up to 6 bp and with maximum total lengths of about 70 bp. Microsatellite dinucleotide repeats are proving to be very powerful tools in the identification of human genes, are highly polymorphic (Weber, 1990, Genomic Analysis, 1:159–181, Cold Spring Laboratory Press, Cold Spring Harbor, N.Y.; Weber and Wong, *Hum. Mol. Genetics*, 2:, 1123, 1993) and may possess up to 24 alleles. Chromosome specific markers which permit a high level of multiplexing have been reported for performing whole genome scans for linkage analysis (Davies et al., *Nature*, 371: 130, 1994).

Repeats can be amplified using primers complementary to the unique regions surrounding the dinucleotide repeat. Following amplification, several amplified loci can be combined (multiplexed) prior to capture on an array.

Genotyping or DNA fingerprinting involves the display of a set of DNA fragments from a specific sample. A variety of DNA fingerprinting techniques are presently available (Jeffreys et al., *Nature*, 314: 67–73, 1985: Zabeau and Vos, European Patent Application 92402629.7.; Vos et al. *Nucl.*

Acids Res. 23: 4407–4414, 1996; Bates et al., in *The Impact of Plant Molecular Genetics*, Chapter 14, pp. 239–255, ed. B.W.S. Sobral, Birkhauser Publishing). DNA fingerprinting involves the display of a set of DNA fragments from a specific DNA sample. A variety of DNA fingerprinting techniques are presently available (Jeffries et al., *Nature* 314:67, 1985; Welsh and McClelland, *Nuc. Acids. Res.* 19:861, 1991), most of which use amplification (e.g., PCR) to generate fragments. The DNA fingerprinting process produces "fingerprint" patterns of different fragment lengths that are characteristic and reproducible for an individual organism. These fingerprints can be use to distinguish even very closely related organisms, including near-isogenic lines. The differences in fragment lengths or sequence can be traced to base changes in the restriction site or the primer extension site, or to insertions or deletions within a DNA fragment.

The choice of which fingerprinting technique to use is dependent on the application, (e.g., DNA typing, DNA marker mapping) and the organisms under investigation, (e.g., prokaryotes, plants, animals, humans). A number of fingerprinting methods which meet these requirements have been developed, including random amplified polymorphic DNA (RAPD), DNA amplification fingerprinting (DAF), and arbitrarily primed PCR (AP-PCR). These methods are all based on the amplification of random genomic DNA fragments by arbitrarily selected PCR primers allowing generation of DNA fragment patterns from any DNA without prior sequence knowledge. The patterns generated depend on the sequence of the amplification primers and the nature of the template DNA. Low annealing temperatures are used to allow the primers to anneal to multiple loci on the DNA, which are amplified when primer binding sites are sufficiently close together. In principle, a single primer is sufficient for generating band patterns.

An additional technique for DNA fingerprinting has been described, named AFLP (Vos et al., *Nuc. Acids Res.* 23:4407, 1995). The AFLP technique is based on the detection of genomic restriction fragments by amplification, and can be used for DNAs of any origin or complexity. Briefly, the technique is based on selective amplification of restriction fragments from a total digest of genomic DNA. The technique involves three steps: 1) restriction of the DNA fragments and subsequent ligation of oligonucleotide adaptors, 2) selective amplification of sets of restriction fragments, 3) analysis of the amplified fragments. Amplification of the restriction fragments is achieved by using the adaptor and restriction site sequence as target sites for primer annealing. The selective amplification is achieved by the use of primers that extend into the restriction fragments, amplifying only those fragments in which the primer extensions match the nucleotides flanking the restriction sites. This method therefore yields sets of restriction fragments which may be visualized by a variety of methods (e.g., PAGE, HPLC, or other types of spectrometry) without prior knowledge of the nucleotide sequence. The method also allows the co-amplification of large numbers of restriction fragments. The number of fragments however is dependent on the resolution of the detection system. Typically, 50–100 restriction fragments are amplified and detected.

An amplification approach to identify restriction fragment length polymorphism (RFLP) combines separation techniques with detection of tags associated with specific PCR primers. In general, one primer will possess one specific tag. The tag will therefore represent one set of primers and therefore a pre-determined DNA fragment length. Polymorphisms are detected as variations in the lengths of the labeled fragments in a gel or eluting from a gel. HPLC or polyacrylamide gel electrophoresis will usually afford the resolution necessary to distinguish minisatellite/VNTR alleles differing by a single repeat unit. Analysis of microsatellite polymorphisms involves amplification by the polymerase chain reaction (PCR) of a small fragment of DNA containing a block of repeats followed by electrophoresis of the amplified DNA on denaturing polyacrylamide gel or followed by separation of DNA fragments by HPLC. The amplified DNA may be labeled using primers that have labels attached. The primers are incorporated into the newly synthesized strands by chain extension. The primers are complementary to unique sequences that flank the blocks of repeats.

Tags can be used to great effect in genotyping with microsatellites. Briefly, the PCR primers are constructed to carry tags and used in a carefully chosen PC reaction to amplify di-, tri-, or tetra-nucleotide repeats. The amplification products are then separated according to size by methods such as HPLC or PAGE. The DNA fragments are then collected in a temporal fashion, the tags cleaved from their respective DNA fragments and length deduced from comparison to internal standards in the size separation step. Allele identification is made from reference to size of the amplified products.

By using cleavable tags in genotyping, it is possible to combine multiple samples on a single separation step. There are two general ways in which this can performed. The first general method for high through-put screening is the detection of a single polymorphism in a large group of individuals. In this scenario, a single or nested set of PCR primers is used and each amplification is done with one DNA sample type per reaction. The number of samples that can be combined in the separation step is proportional to the number of cleavable tags that can be generated per detection technology (i.e., 400–600 for mass spectrometer tags). It is therefore possible to identify several polymorphisms in a large group of individuals simultaneously. The second approach is to use multiple sets of primers which can identify numerous polymorphisms on a single DNA sample (genotyping an individual for example). In this approach, primers are combined in a single amplification reaction which generate amplified products of different sequence. Each primer pair or nested set is encoded by a specific cleavable tag resulting in each amplified fragment encoded with a specific tag. The reaction is run on a single separation step. The number of samples that can be combined in the separation step is proportional to the number of cleavable tags that can be generated per detection technology (i.e., 400–600 for mass spectrometer tags).

B. Mutation detection

The detection of diseases is increasingly important in prevention and treatments. While multifactorial diseases are difficult to devise genetic tests for, more than 200 known human disorders are caused by a defect in a single gene, often a change of a single amino acid residue (Olsen, *Biotechnology: An industry comes of age*, National Academic Press, 1986). Many of these mutations result in an altered amino acid that causes a disease state.

Sensitive mutation detection techniques offer extraordinary possibilities for mutation screening. For example, analyses may be performed even before the implantation of a fertilized egg (Holding and Monk, *Lancet* 3:532, 1989). Increasingly efficient genetic tests may also enable screening for oncogenic mutations in cells exfoliated from the respiratory tract or the bladder in connection with health check-ups (Sidransky et al., *Science* 252:706, 1991). Also, when an unknown gene causes a genetic disease, methods to monitor DNA sequence variants are useful to study the inheritance of disease through genetic linkage analysis. However, detecting and diagnosing mutations in individual genes poses technological and economic challenges. Several different approaches have been pursued, but none are both efficient and inexpensive enough for truly wide-scale application.

Mutations involving a single nucleotide can be identified in a sample by physical, chemical, or enzymatic means. Generally, methods for mutation detection may be divided into scanning techniques, which are suitable to identify previously unknown mutations, and techniques designed to detect, distinguish, or quantitate known sequence variants. Several scanning techniques for mutation detection have been developed based on the observation that heteroduplexes of mismatched complementary DNA strands, derived from wild type and mutant sequences, exhibit an abnormal migratory behavior.

One strategy for detecting a mutation in a DNA strand is by substituting (during synthesis) one of the normal nucleotides with a modified or labeled nucleotide or by altering the molecular weight or other physical parameter of the product. A strand with an increased or decreased number of this modified nucleotide relative to the wild-type sequence exhibits altered mobility (Naylor et al., *Lancet* 337:635, 1991). Heteroduplex DNA molecules generated by amplification, containing internal mismatches, can also be separated from correctly matched molecules by mobility (Orita, *Genomics* 5:874, 1989; Keen, *Trends Genet.* 7:5, 1991), indicating the presence of a mutation in a limited segment of DNA.

Mutations may be also be identified via their destabilizing effects on the hybridization of short oligonucleotide probes to a target sequence (see Wetmur, *Crit. Rev. Biochem. Mol. Biol.*, 26:227, 1991). Generally, this technique, allele-specific oligonucleotide hybridization, involves amplification of target sequences and subsequent hybridization with short oligonucleotide probes. An amplified product can thus be scanned for many possible sequence variants by determining its hybridization pattern to an array of immobilized oligonucleotide probes. Another method exploits the property that an oligonucleotide primer that is mismatched to a target sequence at the 3' penultimate position exhibits a reduced capacity to serve as a primer in PCR. Additional mismatches may be incorporated into the primer at the third position from the 3' end. This results in two mismatched positions in the three 3' nucleotides of the primer hybridized with one allelic variant, and one mismatch in the third position in from the 3' end when hybridized to the other allelic variant (Newton et al., *Nucl. Acids Res.* 17:2503, 1989). Amplification conditions are chosen that significantly favor amplification of a 1 bp mismatch.

C. Expression profiles/differential display

Mammals, such as human beings, have about 100,000 different genes in their genome, of which only a small fraction, perhaps 15%, are expressed in any individual cell. The process of normal cellular growth and differentiation, as well as the pathological changes that arise in diseases like cancer, are all driven by changes in gene expression. Differential display techniques permit the identification of genes specific for individual cell types.

As disclosed herein, a high throughput method for measuring the expression of numerous genes (1–2000) is provided. Within one aspect of the invention methods are provided for analyzing the pattern of gene expression from a selected biological sample, comprising the steps of (a) amplifying cDNA from a biological sample using one or more tagged primers, wherein the tag is correlative with a particular nucleic acid probe and detectable by non-fluorescent spectrometry, or potentiometry, (b) separating amplified fragments, (c) cleaving the tag from the tagged fragment, and (d) detecting the tag by non-fluorescent spectrometry, or potentiometry, and therefrom determining the pattern of gene expression of the biological sample.

Briefly, in differential display, the 3' terminal portions of mRNAs are amplified and identified on the basis of size. Using a primer designed to bind to the 5' boundary of a poly(A) tail for reverse transcription, followed by amplification of the cDNA using upstream arbitrary sequence primers, mRNA sub-populations are obtained. Size separation methods (PAGE, HPLC, etc.) allows direct side by side comparison of lengths or amounts of the mRNAs between two biological samples of interest. The differential display method has the potential to visualize all the expressed genes (about 10,000 to 15,000 mRNA species) in a mammalian cell by using multiple primer combinations.

Tag-based differential display on solid substrates allows characterization of differentially expressed genes. It is based on the principle that most mRNAs expressed in two or more cell types or samples of interest can be directly compared on gels by amplifying partial cDNA sequences from subsets of mRNA with reverse transcription and PCR. Briefly, three one-base anchored oligo-dT primers are used in combination with a series of arbitrary 13 base oligonucleotides to reverse transcribe and amplify the mRNAs from a cell or sample of interest. For monitoring the expression of 15,000 genes, it is preferred that at least nine different arbitrary primers are used. For a complete differential display analysis of two cell populations or two samples of interest, at least 400 amplification reactions are required. With tag-based differential display analysis of two cell types, at least 1500 amplification reactions are easily and quickly performed.

D. Single nucleotide extension assay

The primer extension technique may be used for the detection of single nucleotide in a nucleic acid template (Sokolov, *Nucleic Acids Res.*, 18:3671, 1989). As originally described, 30 base oligonucleotides and 20 base oligonucleotides complementary to the known sequence of the cystic fibrosis gene were extended in the presence of a single labeled nucleotide. The method had the ability to correctly identify a single nucleotide change within the gene. The technique is generally applicable to detection of any single base mutation (Kuppuswamy et al., *Proc. Natl. Acad. Sci. USA*, 88:1143–1147, 1991).

Briefly, this method is based on a primer that hybridizes to a sequence in a target molecule adjacent to a known single nucleotide polymorphism. Within the context of the present invention, the target molecule is preferably covalently attached to the solid substrate. The primed DNA is then subjected to conditions in which a DNA polymerase adds a labeled dNTP, or ddNTP, if the next base in the template is complementary to the labeled nucleotide in the reaction mixture. Free labeled dNTP or ddNTP is washed away, and the extended products are detected.

In a modification of the technique, cDNA is a template for amplification of a sequence of interest containing a single-base difference between two alleles. The amplification products are then printed on the array. Each amplified product is then analyzed for the presence, absence, or relative amounts of each allele by annealing a primer that is 1 base 5' to the polymorphism and extending by one labeled base (generally a dideoxynucleotide). Only when the correct base is available in the reaction will incorporation occur at the 3'-end of the primer. Extension products are then analyzed as above.

In the present invention, each (di)deoxynucleotide is labeled with a unique tag. Of the four reaction mixtures, only one will add a dideoxy-terminator on to the primer sequence. If the mutation is present, it will be detected through the unique tag on the dideoxynucleotide and its identity established. Multiple mutations can be ascertained simultaneously by tagging the DNA primer with a unique tag as well. Thus, the DNA fragments are reacted in four separate reactions each including a different tagged (di) deoxyterminator, wherein the tag is correlative with a particular dideoxynucleotide and detectable by non-fluorescent spectrometry, or potentiometry. The DNA fragments are separated according to size by, for example, gel electrophoresis (e.g., polyacrylamide gel electrophoresis) or preferably HPLC or detected in situ. The tags are cleaved from the fragments and detected by the respective detection technology (e.g., mass spectrometry, infrared spectrometry, potentiostatic amperometry or UV/visible spectrophotometry). The tags detected can be correlated to the particular DNA fragment under investigation as well as the identity of the mutant nucleotide.

E. Oligonucleotide ligation assay

The oligonucleotide ligation assay (OLA) as originally described by Landegren et al. (Landegen et al., *Science* 241:487, 1988) is used for the identification of known sequences in very large and complex genomes. The principle of OLA is based on the ability of ligase to covalently join two diagnostic oligonucleotides as they hybridize adjacent to one another on a given DNA target. If the sequences at the probe junctions are not perfectly based-paired, the probes will not be joined by the ligase. The ability of a thermostable ligase to discriminate potential single base-pair differences when positioned at the 3' end of the "upstream" probe provides the opportunity for single base-pair resolution (Barony, *Proc. Natl. Acad. Sci. USA*, 88:189, 1991). When tags are used, they are attached to the probe, which is ligated to the amplified product. After completion of OLA, unligated oligo nucleotides are removed by incubation at a temperature that melts the unligated oligonucleotides but not the ligated oligonucleotides. Althernatively, fragments are separated on the basis of size. The tags are cleaved and detected by mass spectrometry.

In another embodiment, oligonucleotide-ligation assay employs two adjacent oligonucleotides: a "reporter" probe (tagged at the 5' end) and a 5'-phosphorylated/3' tagged "anchor" probe. The two oligonucleotides, which have incorporated different tags, are annealed to target DNA and, if there is perfect complementarity, the two probes are ligated by T4 DNA ligase. In one embodiment, the 3' tag is biotin and capture of the biotinylated anchor probe on immobilized streptavidin and analysis for the covalently linked reporter probe test for the presence or absence of the target sequences.

Within one embodiment of the invention methods are provided for determining the identity of a nucleic acid molecule, or for detecting a selecting nucleic acid molecule, in, for example a biological sample, utilizing the technique of oligonucleotide ligation assay. Briefly, such methods generally comprise the steps of performing amplification on the target DNA followed by hybridization with the 5' tagged reporter DNA probe and a 5' phosphorylated/non-biotinylated probe. The sample is incubated with T4 DNA ligase. The DNA strands with ligated probes can be separated from the DNA with non-ligated probes by, for example, preferably by LC or HPLC. The tags are cleaved from the separated fragments, and then the tags are detected by the respective detection technology (e.g., mass spectrometry, infrared spectrophotometry, potentiostatic amperometry or UV/visible spectrophotometry.

In the present invention, multiple samples and multiple mutations may be analyzed concurrently. Briefly, the method consists of amplifying the gene fragment containing the mutation of interest. The amplified product is then hybridized with a common and two allele-specific oligonucleotide probes (one containing the mutation while the other does not) such that the 3' ends of the allele-specific probes are immediately adjacent to the 5' end of the common probe. This sets up a competitive hybridization-ligation process between the two allelic probes and the common probe at each locus. The common probe is labeled with one of four fluorophores and the allele-specific probes are each labeled with one or more tags that provide sizing differences. The samples are then separated based upon the length of the modifying tails and detected by the fluorescent tag on the common probe. Through the use in sizing differences on the allele-specific probes and four fluorophores available for the common probe, many samples can be analyzed.

Within one embodiment of the invention methods are provided for determining the identity of a nucleic acid molecule, or for detecting a selecting nucleic acid molecule, in, for example a biological sample, utilizing the technique of oligonucleotide ligation assay for concurrent multiple sample detection. Briefly, such methods generally comprise the steps amplifying target DNA followed by hybridization with the common probe (untagged) and two allele-specific probes tagged according to the specifications of the invention. The sample is incubated with DNA ligase and fragments separated by, for example, preferably by LC or HPLC. The tags are cleaved from the separated fragments, and then the tags are detected by the respective detection technology (e.g., mass spectrometry, infrared spectrophotometry, potentiostatic amperometry or UV/visible spectrophotometry.

F. Other assays

The methods described herein may also be used to genotype or identification of viruses or microbes. For example, F+RNA coliphages may be useful candidates as indicators for enteric virus contamination. Genotyping by nucleic acid amplification and hybridization methods are reliable, rapid, simple, and inexpensive alternatives to serotyping (Kafatos et. al., *Nucleic Acids Res.* 7:1541, 1979). Amplification techniques and nucleic aid hybridization techniques have been successfully used to classify a variety of microorganisms including *E. coli* (Feng, *Mol. Cell Probes* 7:151, 1993), rotavirus (Sethabutr et. al., *J. Med Virol.* 37:192, 1992), hepatitis C virus (Stuyver et. al., *J. Gen Virol.* 74:1093, 1993), and herpes simplex virus (Matsumoto et. al., *J. Virol. Methods* 40:119, 1992).

Genetic alterations have been described in a variety of experimental mammalian and human neoplasms and represent the morphological basis for the sequence of morphological alterations observed in carcinogenesis (Vogelstein et al., *NEJM* 319:525, 1988). In recent years with the advent of molecular biology techniques, allelic losses on certain chromosomes or mutation of tumor suppressor genes as well as mutations in several oncogenes (e.g., c-myc, c-jun, and the ras family) have been observed. For example, a correlation between specific types of point mutations in the K-ras oncogene and the stage at diagnosis in colorectal carcinoma has been identified (Finkelstein et al., *Arch Surg.* 128:526, 1993). Thus, mutational analysis could provide important information of tumor aggressiveness, including the pattern and spread of metastasis. Indeed, the prognostic value of TP53 and K-ras-2 mutational analysis in stage III carcinoma of the colon has been demonstrated (Pricolo et al., *Am. J. Surg.* 171:41, 1996). It is therefore apparent that genotyping of tumors and pre-cancerous cells, as well as specific mutation detection will become increasingly important in the treatment of cancers in humans.

The following examples are offered by way of illustration, and not by way of limitation.

EXAMPLES

Example 1
Preparation of Arraying Tip from a Commercial Spring Probe.

This example describes the manufacture and modification of a spring probe tip for use in depositing samples in an array.

XP54P spring probes are purchased from Osby-Barton (a division of Everett Charles (Pomona, Calif.)). The probes are placed "tip-down" on an extra fine diamond shrpening stone and moved across the stone about 0.5 cm with gentle pressure. Approximately 0.005 inches (0.001 to 0.01 inches) of metal is removed from the end of the tip as observed by microscopy. The tip end is polished by rubbing the tip across a leather strip and then washed with water. Tips are stored dry or stored in 50% glycerol at −20° C. For use in preparation of arrays, the tips are mounted in a head in an array fashion. The head is mounted on an robotic arm, which possesses controllable motion in the z-axis.

Example 2
Preparation of Arrays of Microspheres of Glass Slides.

Figure 1B:
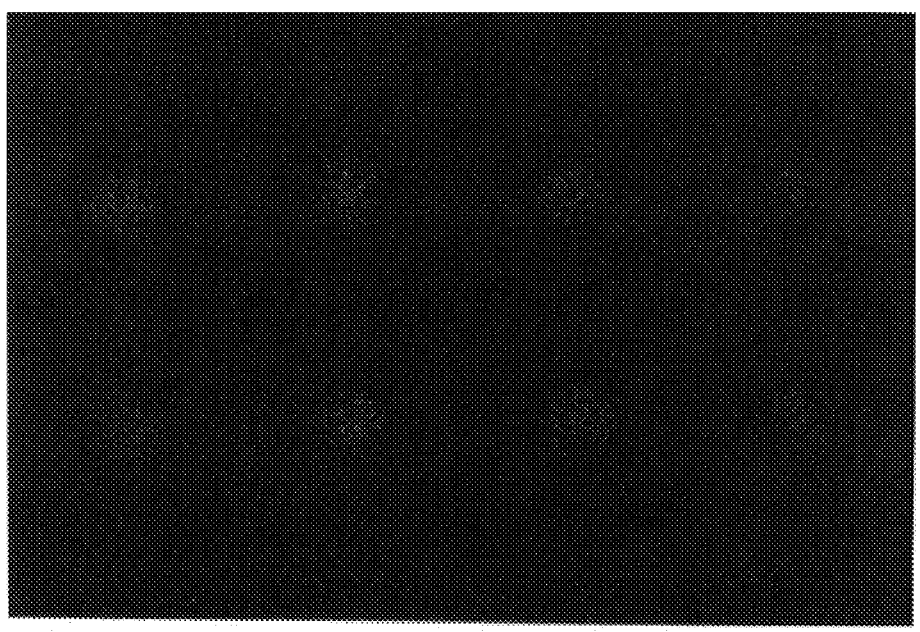

Deposition of easily detectable microspheres on glass slides demonstrates reproducibility of array formation. In this procedure, a solution consisting of 56% glycerol, 0.01 M Tris pH 7.2, 5 mM EDTA, 0.01% sarkosyl, and 1% v/v Fluoresbrite Plain 0.5 $\mu$M microspheres (2.5% solids-latex), (Polysciences, Warrington, Pa.) is prepared. An arraying pin is submerged 5 mm into this solution for 5 sec. The microspheres are then repeatedly arrayed onto a glass slide. Photomicrographs of the slide are taken under fluorescence light using a filter for fluorescence. FIG. 1 demonstrates that the amount of deposited solution in each area of the array is very consistent. Moreover, at least 100 deposits can be made per pickup that are virtually identical.

Example 3
Preparation of as Array Using a Modified Hydrophilic Spring Probe

Sample pick-up, transfer and micro-droplet deposition is greatly enhanced when using a liquid transfer device that has a hydrophilic surface, especially when that device is a modified spring probe. Spring probes are rendered hydrophilic through the use of chemical agents acting to modify the surface of the probe or through coating the probe with a hydrophilic substance. In a preferred method, the tip of the spring probe is soaked in a 25–200 mM solution of 1,4-dithiothreitol, 0.1 M sodium borate for 15 min to 2 hrs. Dithiothreitol reacts with gold surfaces through a thiol-gold coordination, which essentially hydroxylates the surface, making it hydrophilic.

Figure 2:
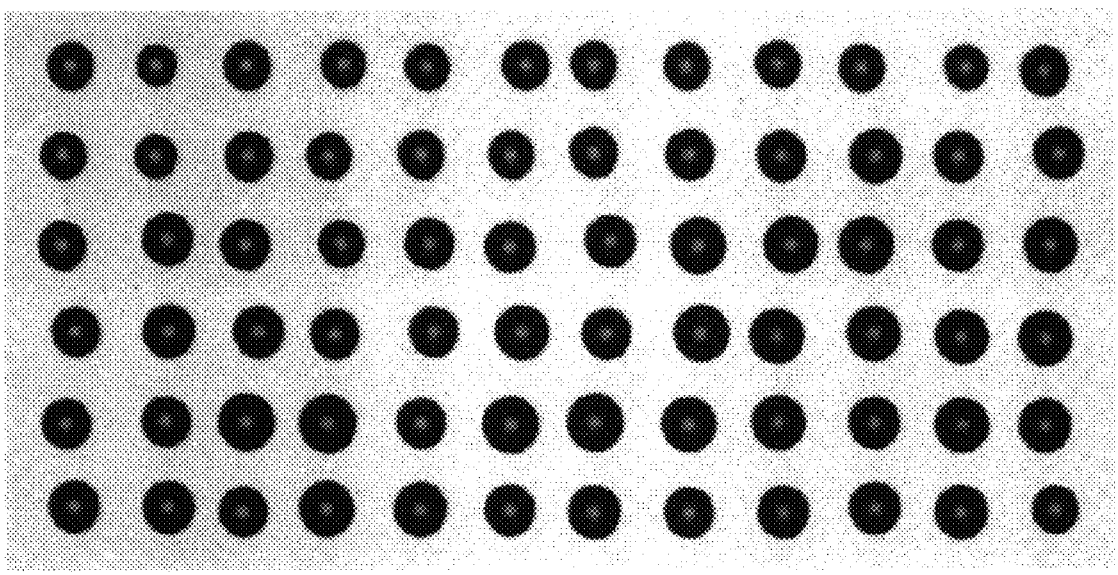
FIG. 2 shows a CCD camera image of an array produced by a robot using the methodology of the invention, where the domains are approximately 100–150 microns in average diameter with 200 micron center to center spacing between spots. The standard deviation of spot diameter is approximately 15%.

An arraying solution is made consisting of 56% glycerol and 44% water colored with blue food color. The arraying tip is submerged 5 mm into the arraying solution for 2 sec. The glycerol bearing tip is then robotically controlled to print 72 microspots in a 12×6 grid onto a silicon wafer. The spots produced were approximately 100–150 microns in diameter with 200 micron center to center spacing between spots. FIG. 2 shows a CCD camera image of the grid produced. The standard deviation of spot diameter is approximately 15%.

Example 4
Colorimetric Detection of Arrayed Oligonucleotides.

Figure 3:
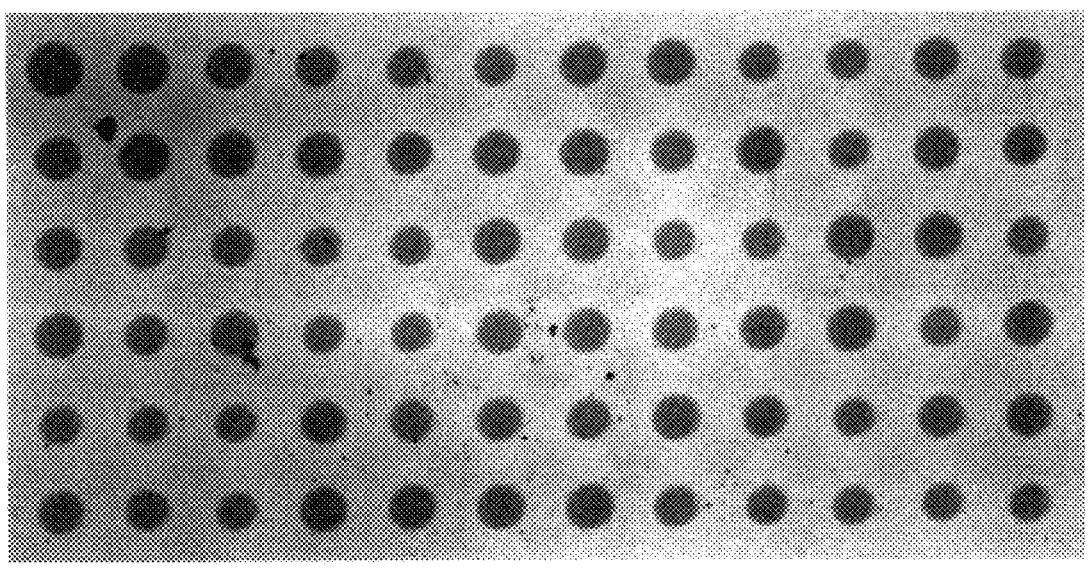
FIG. 3 shows an array of microspots prepared according to the invention and developed using Vector Blue (Vector Laboratories, Burlingame, Calif.) and imaged with a CCD camera and microscope.

Template oligonucleotide (75 $\mu$l of 0.5 $\mu$g/$\mu$l) (5'- hexylamine GTCATACTCCT-GCTTGCTGATCCACATCTG-'3) (SEQ ID NO: 1) is reacted with 5 $\mu$l of a 20 mg/ml cyanuric chloride in 20 $\mu$l of 1 M sodium borate for 30 min at room temperature. From this reaction, an arraying solution is made, which consists of 56% glycerol, 56 ng/ul oligonucleotide, 0.06 mM sodium borate and 0.3 mg/ml cyanuric chloride. The arraying tip is submerged 5 mm into the arraying solution for 2 sec. The solution bearing tip is then robotically controlled to print 72 microspots in a 12×6 grid onto a polyethyleneimine (PEI) coated silicon wafer. The spots produced are approximately 100–150 microns in diameter with 200 micron center to center spacing between spots. Following arraying, the unreacted PEI sites on the wafer are blocked with 100 mg/ml succinic anhydride in 100% n-methyl pyrrolinidone for 15 minutes followed by 3 washes in water. The unreacted cyanuric chloride sites are blocked with 0.1 M glycine in 0.01 M Tris for 15 minutes with four washes in Tens buffer (0.1 M NaCl, 0.1% SDS, 0.01 M Tris, 5 mM EDTA). The template oligomer is then hybridized to its biotinylated complement (5'-Biotin-TGTGGATCAGCAAGCAGGAGTATG-3') (SEQ ID NO:2) for 20 min at 37° C. followed by a wash in 6× Tens and 2× OHS (0.06 M Tris, 2 mM EDTA, 5× Denhardt's solution, 6× SSC [3 M NaCl, 0.3 M sodium citrate, pH 7.0], 3.68 mM N-lauroylsarcosine, 0.005% NP-40). The wafer is then soaked in 0.5 $\mu$g/ml alkaline phosphatase conjugated streptavidin for 15 min followed by a wash in 2× Tens, 4× TWS (0.1 M NaCl, 0.1% Tween 20, 0.05 M Tris). The microspots are then developed using Vector Blue (Vector Laboratories, Burlingame, Calif.) (following kit protocol) and imaged with a CCD camera and microscope. FIG. 3 displays the image generated. The resulting microspots have approximately a 15% variation in diameter and intensity values varying approximately 10% as determined by NIH Image (National Institute of Health, Bethesda, Md.).

Example 5
Multiple Oligos Within a Single Array Element

Two template oligos (#1, 5'-hexylamine-TGTGGATCAGCAAGCAGG AGTATG-3'(SEQ ID NO:2), #2 5'-hexylamine-ACTACTGATCAGGCGCGCCTTTTTTTTTTTTTT TTTT-3') (SEQ ID NO:3) at 0.5 $\mu$g/$\mu$l are reacted seperately with 5 $\mu$l of 20 mg/ml cyanuric chloride and 20 $\mu$l of 1M sodium borate in a total reaction volume of 100 $\mu$l for 30 minutes at room temperature. From these two reactions, arraying solutions are made of 56% glyceroland diluted combinations of the two reacted oligos (see Table below). Eight arraying tips are submerged 5 millimeters into each of the eight arraying solutions for 2 seconds. The solution bearing tips are robotically controlled to print two sets of eight 12×6 grids each containing 72 microspots onto a polyethyleneimine (PEI) coated silicon wafer. Each grid represents a single arraying solution. The spots produced are approximately 100–150 microns in diameter with 200 micron center to center spacing between spots.

Following arraying, the unreacted PEI sites on the wafer are blocked with 100 mg/ml succinic anhydride in 100% n-methyl pyrrolinidone for 15 minutes with a 3× water wash. The unreacted cyanuric chloride sites are blocked with 0.1 M glycine in 0.01 M Tris for 15 minutes with a 4× Tens (0.1 M NaCl, 0.1% SDS, 0.01 M Tris, 5 mM EDTA) wash. Two hybridizations are then carried out. In the first hybridization, one set of the eight arrayed oligo combinations is hybridized to the oligonucleotide, 5'-Biotin- TGTGGATCAGCAAGCAGGAGTATG-3'(SEQ ID NO: 2), which is complementry to oligo #1. In the second hybridization, the other set of the eight arrayed oligo combinations is hybridized to the oligonucleotide (5'-BIOTIN-AAAAAA AAAAAAAAAAAAAAGGCGCGCCTGATCAGTAGT) (SEQ ID NO:4), which is complementry to oligo #2. The hybridizations are conducted simultaneously under Hybriwell Sealing Covers (Research Products International Corporation, Mount Prospect, Ill.) for 20 minutes at 37° C. followed by a 6× Tens, 2× OHS (0.06 M Tris, 2 mM EDTA, 5× Denhardt's solution, 6× SSC (3 M NaCl, 0.3 M sodium citrate, pH 7.0), 3.68 mM N-lauroylsarcosine, 0.005% NP-40) wash. Following hydridization, the wafer is soaked in 0.5 µg/ml horseradish peroxidase streptavidin for 15 minutes followed by a 2× Tens, 4× TWS (0.1 M NaCl, 0.1% Tween 20, 0.05 M Tris) wash. The microspots are then developed using 0.4 mg/ml 4-methoxy 1-napthol (0.02% hydrogen peroxide, 12% methanol, PBS) with a final 3× water wash.

Figure 4:
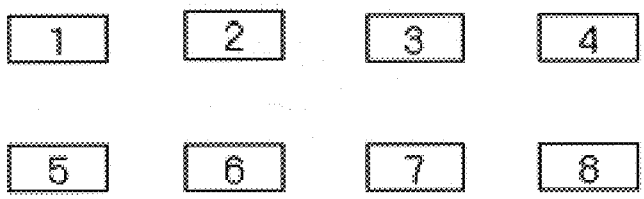
FIG. 4 is an illustration showing how two different oligonucleotides, both present within a single array element, may be identified and partially quantified according to the present invention.
Figure 4:
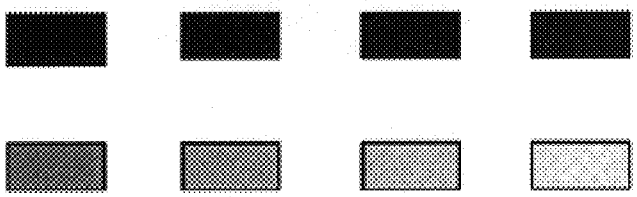
Figure 4:
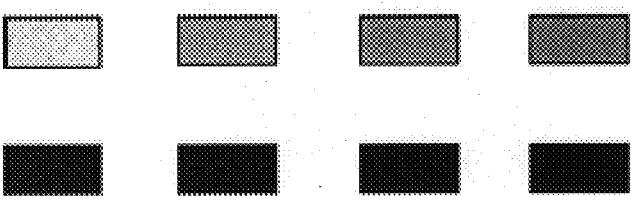

The set of mixed oligos that hybridize to the complement of oligo #1 show the greatest color intensity for the grid containing the highest concentration of oligo #1 and the least color intensity with the grid containing the lowest concentration of oligo #1. Whereas, the set of mixed oligos hybridized to the complement of oligo #2, showed the greatest color intensity for the grid containing the highest concentration of oligo #2 and the least color intensity with the grid containing the lowest concentration of oligo #2 (see FIG. 4).

| Arraying Solution | Concentration of oligo #1 in arraying solution (ng/µl) | Concentration of oligo #2 in arraying solution (ng/µl) |
|---|---|---|
| 1 | 56 | 0.44 |
| 2 | 28 | 0.88 |
| 3 | 14 | 1.8 |
| 4 | 7 | 3.5 |
| 5 | 3.5 | 7 |
| 6 | 1.8 | 14 |
| 7 | 0.88 | 28 |
| 8 | 0.44 | 56 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of amplifying nucleic acid molecules from a template in a chamber, comprising:
   (a) mixing single-stranded nucleic acid templates on a solid substrate with a solution comprising an oligonucleotide primer that hybridizes to the templates and a DNA polymerase, wherein the mixing occurs in discrete areas on the substrate, and wherein the solution remains in the discrete areas;
   (b) synthesizing a complementary strand to the template to form a duplex;
   (c) denaturing the duplex; and
   (d) synthesizing complementary strands to the template, therefrom amplifying nucleic acid molecules;
   wherein the nucleic acid solution is in contact with the atmosphere in the chamber, and dew point is maintained during said mixing, synthesizing, and denaturing, thereby preventing evaporation of the solution.

2. A method of amplifying nucleic acid molecules from a template in a chamber, comprising:
   (a) mixing single-stranded nucleic acid templates on a solid substrate with a solution comprising a first oligonucleotide primer that hybridizes to the templates, a second oligonucleotide primer that hybridizes to a complementary strand of the template, and a DNA polymerase, wherein the mixing occurs in discrete areas on the substrate, and wherein the solution remains in the discrete areas;
   (b) synthesizing a complementary strand to the template to form a duplex;
   (c) denaturing the duplex; and
   (d) synthesizing complementary strands to the template and the complementary strand of the template, therefrom amplifying nucleic acid molecules;
   wherein the solution is in contact with the atmosphere in the chamber, and dew point is maintained during said mixing, synthesizing, and denaturing, thereby preventing evaporation of the solution.

3. The method of either of claims 1 or 2, wherein steps (c) and (d) are performed multiple times.

4. The method of claim 3, wherein steps (c) and (d) are performed from about 10 to about 25 times.

5. The method of either of claims 1 or 2, wherein the solution contains a compound that confers viscosity.

6. The method of claim 5, wherein the compound is glycerol or a sugar.

7. The method of claim 6, wherein the compound is glycerol.

8. The method of claim 6, wherein the compound is a sugar.

9. The method of either of claims 1 or 2, wherein the DNA polymerase is a thermostable polymerase.

10. The method of either of claims 1 or 2, wherein synthesis and denaturation are performed at different temperatures.

11. The method of either of claims 1 or 2, further comprising detecting the duplexes.

12. The method of claim 11, wherein the oligonucleotide primers are labeled.

13. The method of claim 12, wherein the label is a fluorescent molecule.

14. The method of claim 12, wherein the label is a tag that is detectable by non-fluorescent spectrometry or potentiometry.

15. The method of claim 14, wherein the detection of the tag is by mass spectrometry, infrared spectrometry, ultraviolet spectrometry, or poteniostatic amperometry.

16. The method of claim 14, wherein the sequence and the tag of the first or second or both oligonucleotide primers is different for each template.

17. The method of claim 16, wherein the amplified nucleic acids are pooled prior to detection.

18. The method of either of claims 1 or 2, wherein the array is on a solid substrate comprising a silicon wafer or borosilicate slide.

19. The method of claim 18, wherein the templates are covalently attached to the solid substrate.

20. The method of claim 19, wherein the attachment is through a polyethylene imine linkage.

21. The method of claim 2, wherein the oligonucleotide primer pairs each have a different sequence.

22. The method of either of claims 1 or 2, wherein the template is uniformly applied to the entire array prior to mixing.

23. The method of either of claims 1 or 2, wherein the template is applied individually to each discrete area on the substrate.

24. The method of claim 23, wherein the applying is performed using spring probes.

25. The method of either of claims 1 or 2, wherein an apparatus is used to control the dew point.

26. A method of synthesizing a nucleic acid molecule from a template, comprising:
   (a) mixing single-stranded nucleic acid templates on a solid substrate with a solution comprising an oligonucleotide primer that hybridizes to the templates and a DNA polymerase, wherein the mixing occurs in a discrete area of an array, and wherein the solution remains in discrete areas; and
   (b) synthesizing a complementary strand to the template to form a duplex,
   wherein mixing and synthesis are performed at dew point,
   wherein dew point is achieved by an apparatus, comprising: a container capable of being pressurized; a heating device; a means for generating pressure; and a means for generating saturated steam;
   wherein the heating device, pressure generating means, and steam genearting means are controllable.

27. A method of detecting a single base alteration in a nucleic acid molecule, comprising:
   (a) mixing single-stranded nucleic acid molecules on a solid substrate with a solution comprising a first and a second oligonucleotides that hybridize to the nucleic acid molecules and a DNA ligase, wherein the mixing occurs in a discrete area of an array, and wherein the solution remains in the discrete areas; and (b) detecting a ligation product;

wherein the first and second oligonucleotides will not ligate when there is a single base alteration at the junction base on the nucleic acid molecule, p1 mixing is performed at dew point, wherein dew point is achieved by an apparatus, comprising: a container capable of being pressurized; a heating device; a means for generating pressure; and a means for generating saturated steam;

wherein the heating device, pressure generating means, and steam generating means are controllable.

28. A method of performing single nucleotide extension assay, comprising:

(a) mixing oligonucleotides on a solid substrate with a solution comprising single-stranded nucleic acid molecules that hybridize to the oligonucleotides, a single nucleotide, and a DNA polymerase, wherein the mixing occurs in discrete areas of the substrate, and wherein the solution remains in discrete areas; and (b) detecting an extension product of the oligonucleotide;

wherein the oligonucleotide will be extended only when the single nucleotide is complementary to the nucleotide adjacent to the hybridized oligonucleotide, wherein mixing is performed at dew point, wherein dew point is achieved by an apparatus, comprising: a container capable of being pressurized; a heating device; a means for generating pressure; and a means for generating saturated steam;

wherein the heating device, pressure generating means, and steam generating means are controllable.

29. The method of claim 26 wherein step (b) is performed multiple times.

30. The method of claim 26 wherein the solution contains a compound that increases the viscosity of the solution.

31. The method of claim 30 wherein the compound is glycerol or a sugar.

32. The method of claim 30 wherein the array is located on a substantially flat surface of a substrate.

33. The method of claim 32 wherein the substrate is glass.

34. The method of claim 27 wherein the solution contains a compound that increases the viscosity of the solution.

35. The method of claim 34 wherein the compound is glycerol or a sugar.

36. The method of claim 27 wherein the nucleic acid molecules form an array on the substrate, and the array is located on a substantially flat surface of the substrate.

37. The method of claim 36 wherein the substrate is glass.

38. The method of claim 28 wherein the solution contains a compound that increases the viscosity of the solution.

39. The method of claim 38 wherein the compound is glycerol or a sugar.

40. The method of claim 28 wherein the oligonucleotides form an array on the substrate, and the array is located on a substantially flat surface of the substrate.

41. The method of claim 40 wherein the substrate is glass.

* * * * *

UNITED STATES PATENT AND TRADEMARK OFFICE
CERTIFICATE OF CORRECTION

PATENT NO. : 6,248,521 B1
DATED : June 19, 2001
INVENTOR(S) : Jeffrey Van Ness et al.

It is certified that error appears in the above-identified patent and that said Letters Patent is hereby corrected as shown below:

<u>Title page,</u>
Item [56], References Cited, page 2 of the Issued Patent, reference "cmgm.stanford.edu/pbrown/mguide, Sep. 12, 2000 and emgm.stanford.edu/pbrown/mguide/tips. Sept. 12, 2000." should read -- http://cmgm.stanford.edu/pbrown/mguide, 09/12/00 and http://cmgm.stanford.edu/pbrown/mguide/tips.html, 09/12/00 --.

<u>Column 25, claim 27,</u>
Line 9, "molecule, p l mixing" should read -- molecule, wherein mixing --.

Signed and Sealed this

Fifth Day of March, 2002

*Attest:*

*Attesting Officer*

JAMES E. ROGAN
*Director of the United States Patent and Trademark Office*

SEQUENCE LISTING

<160> NUMBER OF SEQ ID NOS: 4

<210> SEQ ID NO: 1
<211> LENGTH: 30
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 1
gtcatactcc tgcttgctga tccacatctg                                      30

<210> SEQ ID NO: 2
<211> LENGTH: 24
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 2
tgtggatcag caagcaggag tatg                                            24

<210> SEQ ID NO: 3
<211> LENGTH: 38
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 3
actactgatc aggcgcgcct tttttttttt tttttttt                             38

<210> SEQ ID NO: 4
<211> LENGTH: 39
<212> TYPE: DNA
<213> ORGANISM: Artificial Sequence

```
-continued

<220> FEATURE:
<223> OTHER INFORMATION: Description of Artificial Sequence: Product of
      Solid Phase Synthesis

<400> SEQUENCE: 4
aaaaaaaaaa aaaaaaaaaa ggcgcgcctg atcagtagt                              39
```